United States Patent

Okafuji et al.

[11] Patent Number: 5,387,978
[45] Date of Patent: Feb. 7, 1995

[54] FLAW DETECTION SYSTEM FOR LIGHT-TRANSMITTING PLATE MATERIAL

[75] Inventors: Masaharu Okafuji; Nagayoshi Ichise, both of Osaka; Mitsuo Odawara; Junichi Abe, both of Kitakyushu, all of Japan

[73] Assignee: Nippon Sheet Glass Co, Ltd., Osaka, Japan

[21] Appl. No.: 26,606

[22] Filed: Mar. 5, 1993

[30] Foreign Application Priority Data

Mar. 6, 1992 [JP] Japan .................. 4-049448

[51] Int. Cl.⁶ .................................... G01N 21/01
[52] U.S. Cl. .................... 356/431; 356/239; 356/237
[58] Field of Search ........... 356/431, 430, 429, 237, 356/239

[56] References Cited

U.S. PATENT DOCUMENTS

| | | | |
|---|---|---|---|
| 3,980,891 | 9/1976 | Slaker | 356/237 |
| 4,724,481 | 2/1988 | Nishioka | 356/237 |
| 4,914,309 | 4/1990 | Masaharu et al. | 356/431 |
| 5,104,523 | 4/1992 | Masaharu et al. | 356/431 |

FOREIGN PATENT DOCUMENTS 0315697 5/1989 European Pat. Off. .

OTHER PUBLICATIONS

European Search Report (93 30 1579) dated Jun. 16, 1993.
M. V. Klein, *Optics*, Second Edition, John Wiley & sons, pp. 476–479.

*Primary Examiner*—Rolf Hille
*Assistant Examiner*—Alexander Oscar Williams
*Attorney, Agent, or Firm*—Ratner & Prestia

[57] ABSTRACT

A flaw detection system that can detect not only bubbles, stones and knots but also flaws, such as cords and reams, that are subject to less optical changes in transmitted light is provided. A glass plate travelling in a manufacturing line is scanned with a beam spot in the direction orthogonally intersecting the manufacturing line. The light transmitted through the glass plate is received by an optical-fiber array arranged in a direction orthogonally intersecting the line. Optical fibers in the optical-fiber array are connected cyclically to a plurality of photomultipliers, which convert the light received by the optical fibers into electrical signals. Flaw signals are produced by extracting flaw information signals from these electrical signals in an analog processing section, and masking them in a masking section. Positional information indicating flaw patterns and positions is produced from these flaw signals.

7 Claims, 15 Drawing Sheets

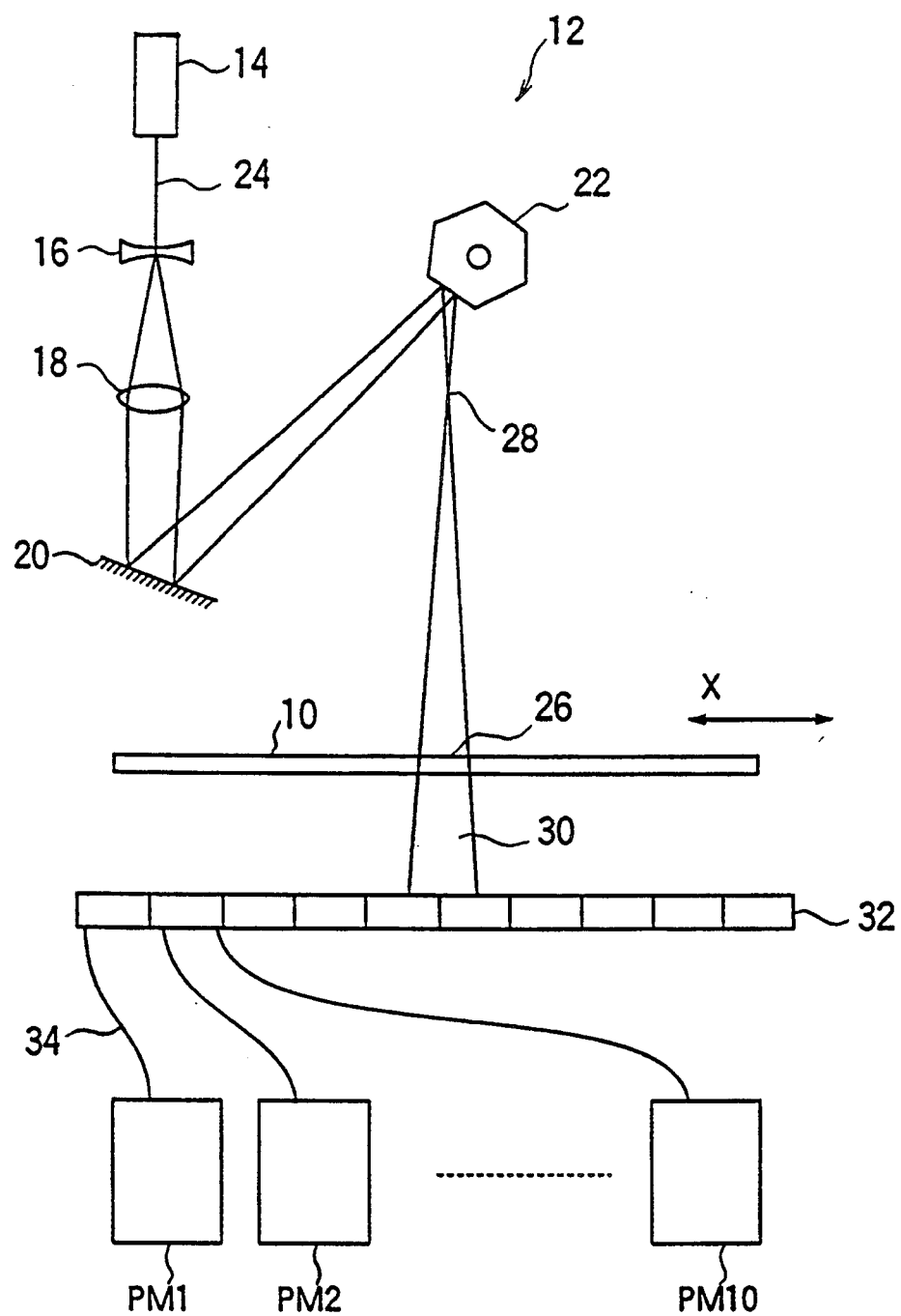
F I G. 1

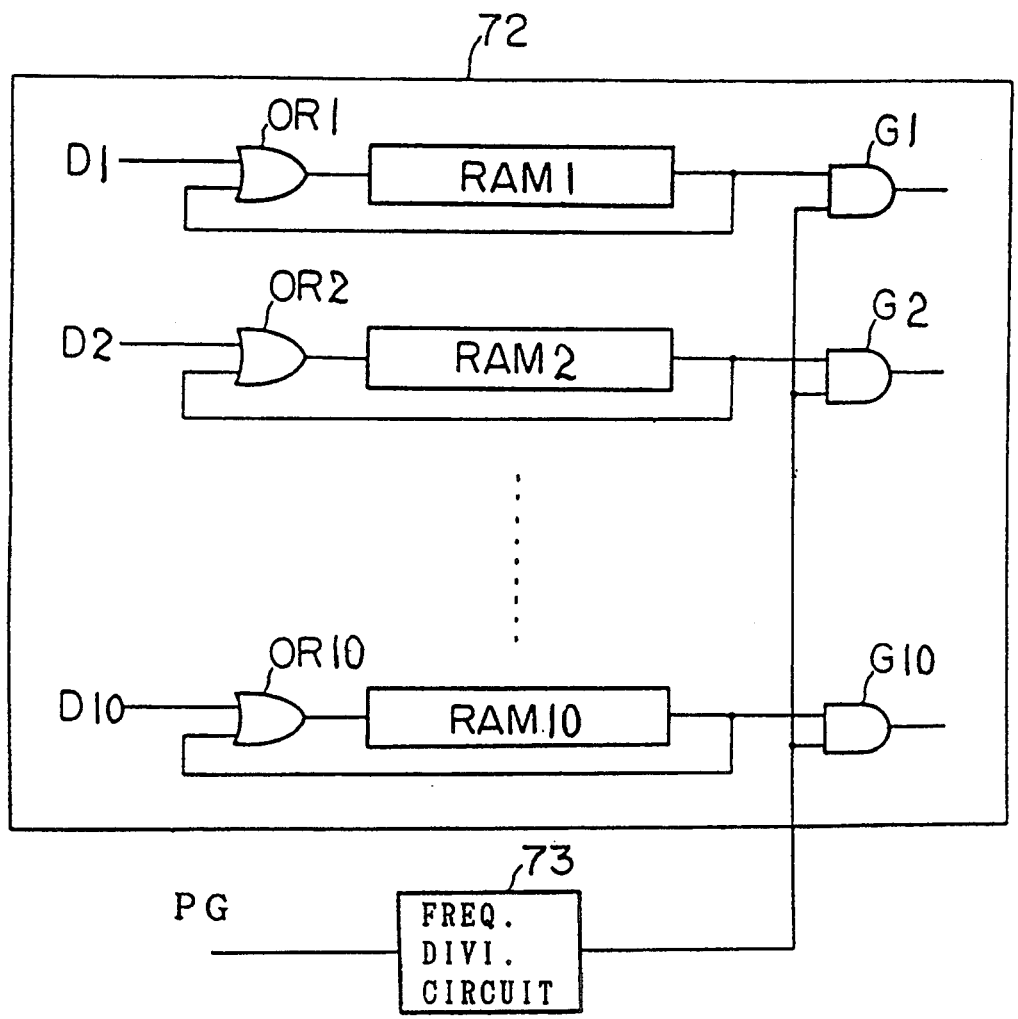
F I G. 1 1

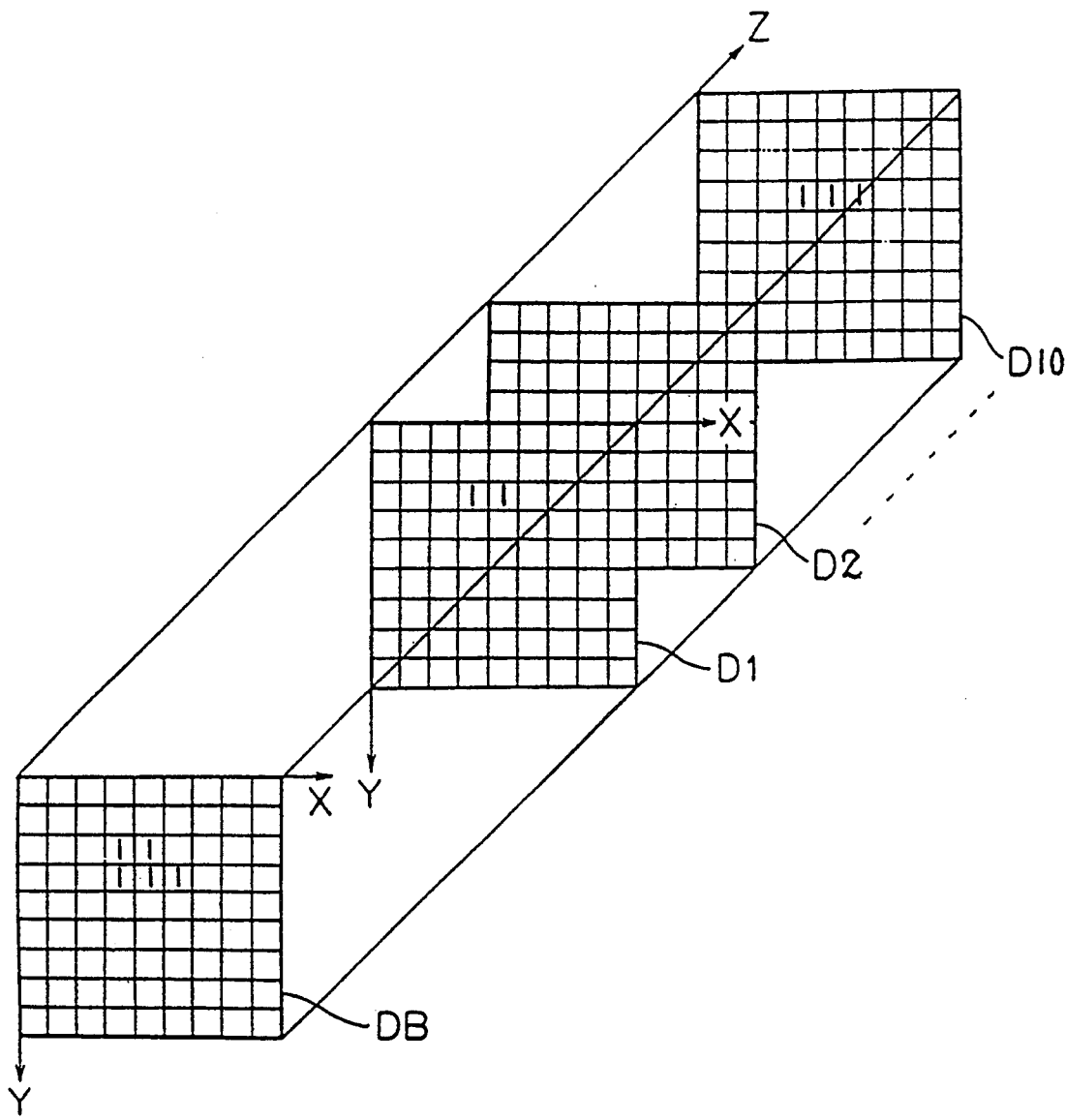
F I G. 1 4

FLAW DETECTION SYSTEM FOR LIGHT-TRANSMITTING PLATE MATERIAL

BACKGROUND OF THE INVENTION

1. Field of the Invention

This invention relates to a flying-spot type flaw detection system for detecting flaws existing in glass plate, plastic plate, or at least a plate material that transmits light (hereinafter referred to as a light-transmitting plate material) by scanning the light-transmitting plate material with a laser-light spot.

2. Description of the Prior Art

The flaw detection system for detecting flaws existing in a light-transmitting material is needed in a glass-plate manufacturing line, for example, to detect flaws present in glass plate being manufactured and feed back the detection results to the transparent glass plate manufacturing process, thereby preventing the recurrence of flaws at positions where they occur and improve product yield. Flaws in glass plate include bubbles formed by air bubbles remaining inside the glass plate, stones produced by foreign matter remaining in the glass plate, knots formed by almost molten foreign matter remaining inside the glass plate in a shape having streaming tail, cords which are knots having a very small width (0.1–0.2 mm), reams formed by the difference in refractive index caused by the difference in glass composition due to improper melting, etc.

Among flaw detection systems of conventional types included is a flying-spot type flaw detection system that scans glass plate with a light spot to detect with a light receptor changes in the optical axis of the transmitted light.

The flaw detection system of the conventional type has a high sensitivity only to changes in transmitted light in the direction of the manufacturing line. Since bubbles, knots and stones, which account for a great majority of flaws in glass plate, tend to cause significant changes in the light transmitted both in the direction of the manufacturing line and in the direction orthogonally intersecting the manufacturing line, they can be detected with the flying-spot flaw detection system of the conventional type. Flaws like cords and reams, however, cause no attenuation in the amount of transmitted light, resulting in very little changes in the light transmitted in the direction of the manufacturing line (about 1/100 as small as the changes in the case of bubbles). In addition, cords and reams, which are usually elongated in the direction of the line, cause changes only in the direction orthogonally intersecting the line. Thus, these flaws are hard to detect with the flying-spot flaw detection system of the conventional type.

It is an object of this invention to provide a flaw detection system that can detect not only flaws involving less optical changes, as represented by cords and reams, but also bubbles, knots, stones, etc.

SUMMARY OF THE INVENTION

The present inventor and others discovered that changes in the pattern of transmitted light are manifested more pronouncedly, that is, changes in the light transmitted in the direction orthogonally intersecting the line become larger by placing the beam waist of a laser beam on the side of the light source when detecting cords involving less optical changes, and by placing the beam waist of a laser beam on the side of the light receptor when detecting reams. They also discovered that the pattern of transmitted light having changes in the transmitted light can best be obtained in real time by using as the light receptor an optical-fiber array arranged in the direction orthogonally intersecting the line, and converting the light signals into electrical signals by means of a plurality of photomultipliers connected cyclically to optical fibers of the optical-fiber array.

Consequently, the flaw detection system for light-transmitting plate materials of this invention is characterized in that the flaw detection system comprises a scanner for scanning a travelling light-transmitting plate material with a beam spot in the direction orthogonally intersecting the travelling direction of the material, a light receptor for receiving the light transmitted through the light-transmitting plate material, having an optical-fiber array in which multiple optical fibers are arranged linearly in the direction orthogonally intersecting the travelling direction of the material, and n (n being an integer more than 2) units of photoelectric converters to which optical fibers in each of a plurality of divisions of the optical-fiber array, obtained by dividing the optical-fiber array into n pieces of fibers, are connected cyclically.

BRIEF DESCRIPTION OF THE DRAWINGS

FIG. 1 is a structural diagram illustrating the optical system of an embodiment of the flaw detection system according to this invention.

FIG. 11 is a diagram illustrating an example of an OR unit.

FIG. 14 is a diagram of assistance in explaining the concept of the operation of a flaw data compression section compressing flaw data.

DETAILED DESCRIPTION OF A PREFERRED EMBODIMENT

Figure 2:
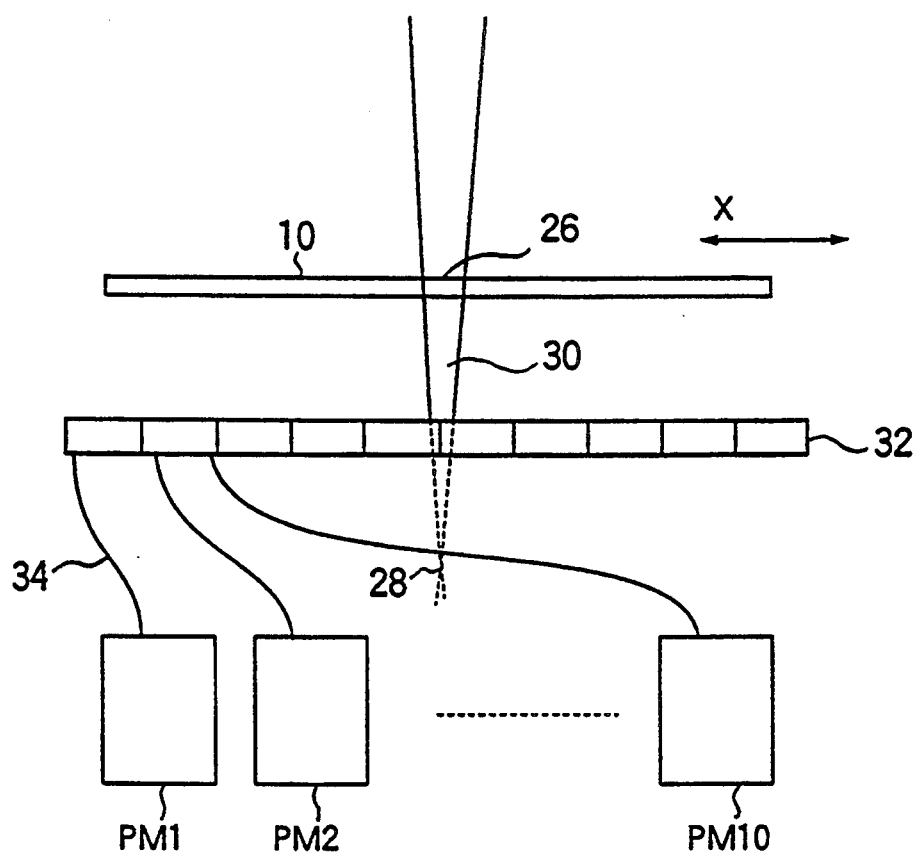
FIG. 2 is a structural diagram illustrating the optical system of another embodiment of the flaw detection system according to this invention.

FIG. 1 is a structural diagram of a flaw detection system embodying this invention. Glass plate 10 travels in the direction perpendicular to the plane of FIG. 1. The travelling direction (line direction) of the glass plate 10 is hereinafter referred to as the Y-axis direction, and the direction orthogonally intersecting the travelling direction of the glass plate 10 as the X-axis direction.

Above the glass plate 10 provided is a laser-spot scanner 12, which comprises a laser 14, a concave lens 16, a convex lens 18, a reflecting mirror 20 and a polygonal rotating mirror 22. A laser beam 24 emitted from the laser 14 falls on the polygonal rotating mirror 22 via the concave lens 16, the convex lens 18 and the reflecting mirror 20. The polygonal rotating mirror 22 that rotates at high speed shifts the laser beam 24 to the X-axis direction, causing a beam spot 26 to scan the top planar surface of the glass plate 10. In this embodiment, the optical system of the scanner 12 is adjusted so that a beam waist 28 of the laser beam 24 is located above the glass plate 10. The diameter of the beam spot 26 is 1–3 mm, for example.

Beneath the bottom planar surface of the glass plate 10 provided is a light receptor 32 receiving a transmitted light beam whose luminous fluxes diffuse. The light receptor 32 comprises an optical-fiber array in which multiple optical fibers 34 are arranged linearly in the X-axis direction so that one end faces of the optical fibers 34 face towards the glass plate 10, with the other ends of the optical fibers being led to a plurality of (10 in this embodiment) photomultipliers PM1–PM10. In the interests of simplicity, only part of the optical fibers 35 are shown in the figure. The diameter of the laser beam received by the light receptor 32 is 4–10 mm, for example.

FIG. 2 shows an example in which the optical system of the scanner 12 is adjusted so that the beam waist 28 of the laser beam 24 is located below the light receptor 32. In this case, the light receptor 32 receives a transmitted light beam whose luminous fluxes converge.

The flaw detection system shown in FIG. 1 is suitable for detecting flaws, such as bubbles, stones, knots and cords, whereas the flaw detection system shown in FIG. 2 is suitable for detecting flaws, such as reams.

Figure 3:
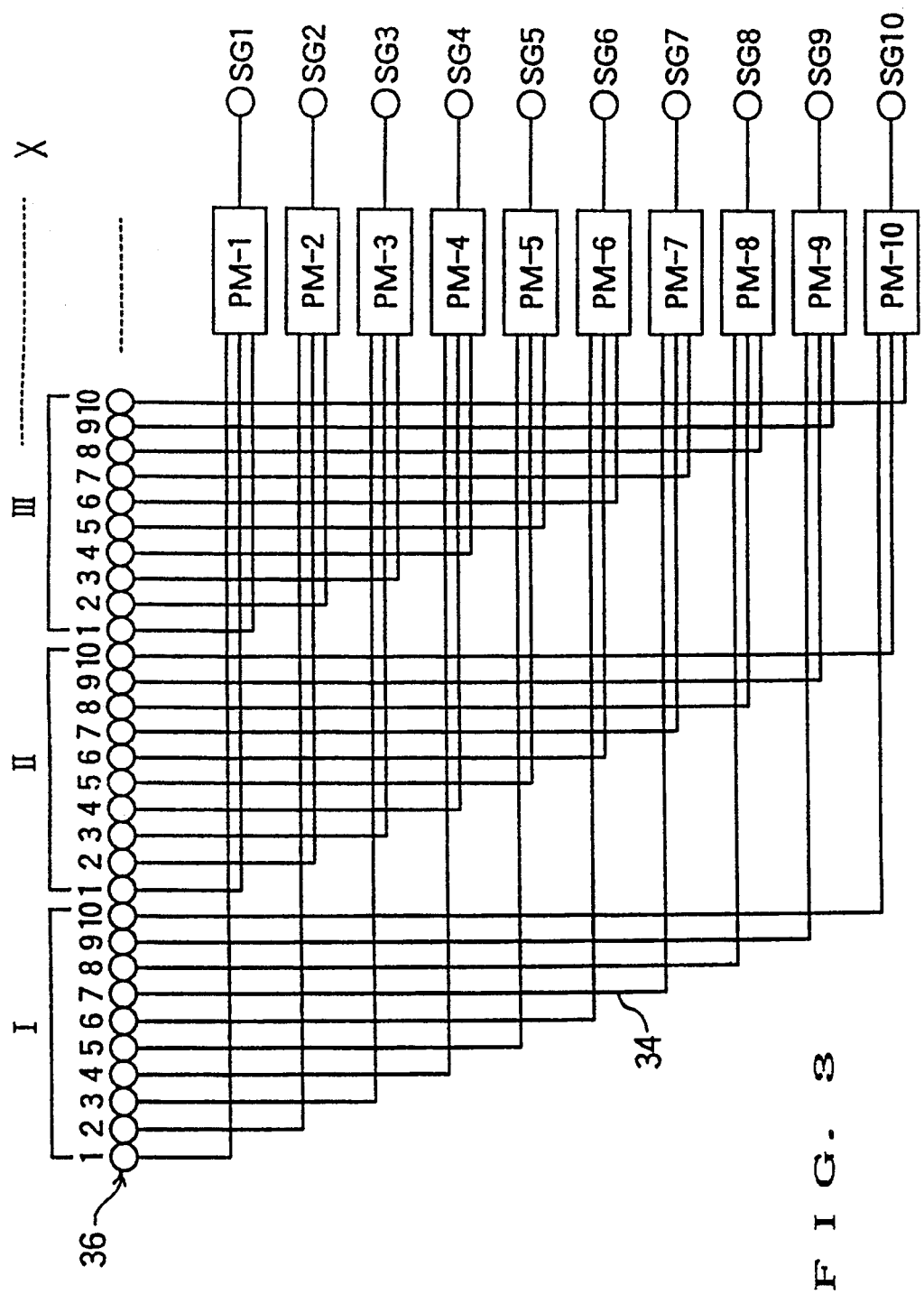
FIG. 3 is a diagram illustrating connections between the light receptors and the photomultipliers.

FIG. 3 shows connections between the light receptor 32 and the photomultipliers PM1–PM10 shown in FIGS. 1 and 2. The optical fiber array 36 constituting the light receptor 32 comprises 100 optical fibers arranged linearly at 1-mm spacings. The optical-fiber array 36 is divided into I, II, III, - - -, X divisions each consisting of 10 optical fibers. When the optical fibers in each division are labeled as Nos. 1-10, the No. 1 optical fiber of each division is connected cyclically to the photomultiplier PM1, the No. 2 optical fiber of each division is to the photomultiplier PM2, - - -, and the No. 10 optical fiber of each division to the photomultiplier PM10, respectively.

The laser beam received by the light receptor 32 is sent to the photomultipliers PM1–PM10 and converted into electrical signals. The electrical signals output by the photomultipliers PM1–PM10 are referred to as SG1–SG10.

Figure 4A:
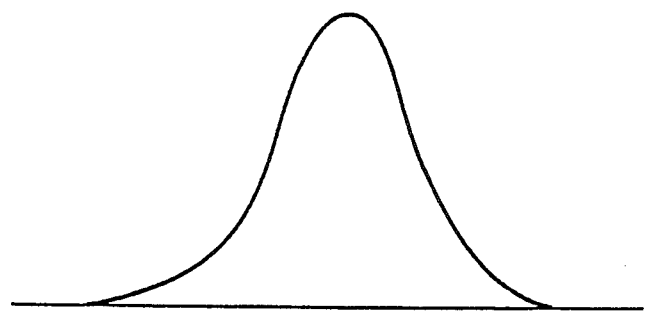
FIGS. 4A and 4B are diagrams illustrating the light-intensity distribution of transmitted light where no flaws exist and where flaws exist.

With reference to the flaw detection system shown in FIG. 1, the light-intensity distribution of the transmitted light received by the light receptor 32 when detecting flaws present in the glass plate 10, such as "cords," involving less optical changes will be described in the following. Where no flaws exist, the light intensity of the transmitted light assume a Gaussian distribution, as shown in FIG. 4A. Where a "cord" flaw exists, the transmitted light changes in the X-axis direction, assuming a light-intensity distribution having a spike, as shown FIG. 4B. In this case, the amount of received light remains unchanged. Where a "bubble," "stone," or "knot" flaw exists in the glass plate 10, the transmitted light remarkably changes in the X-axis direction.

Figure 4B:
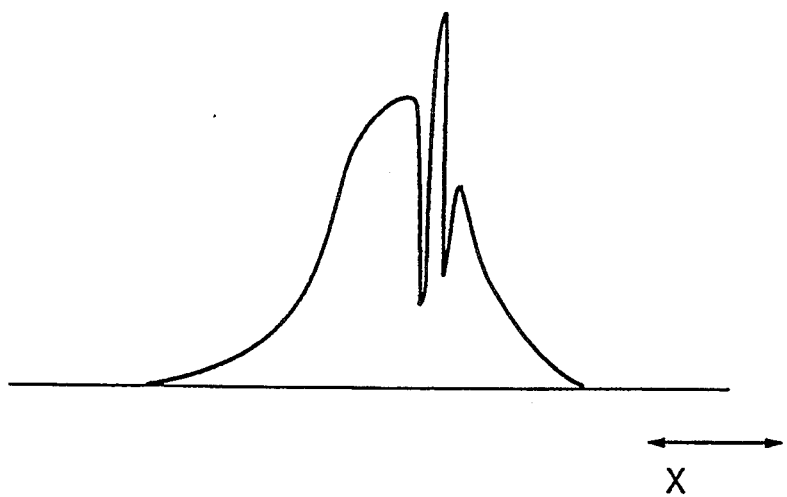

When there is a flaw that involves less optical changes, such as a ream, the transmitted light detected by the flaw detection system shown in FIG. 2 changes in the X-axis direction, assuming a light-intensity distribution having a spike, as shown in FIG. 4B.

Figure 5:
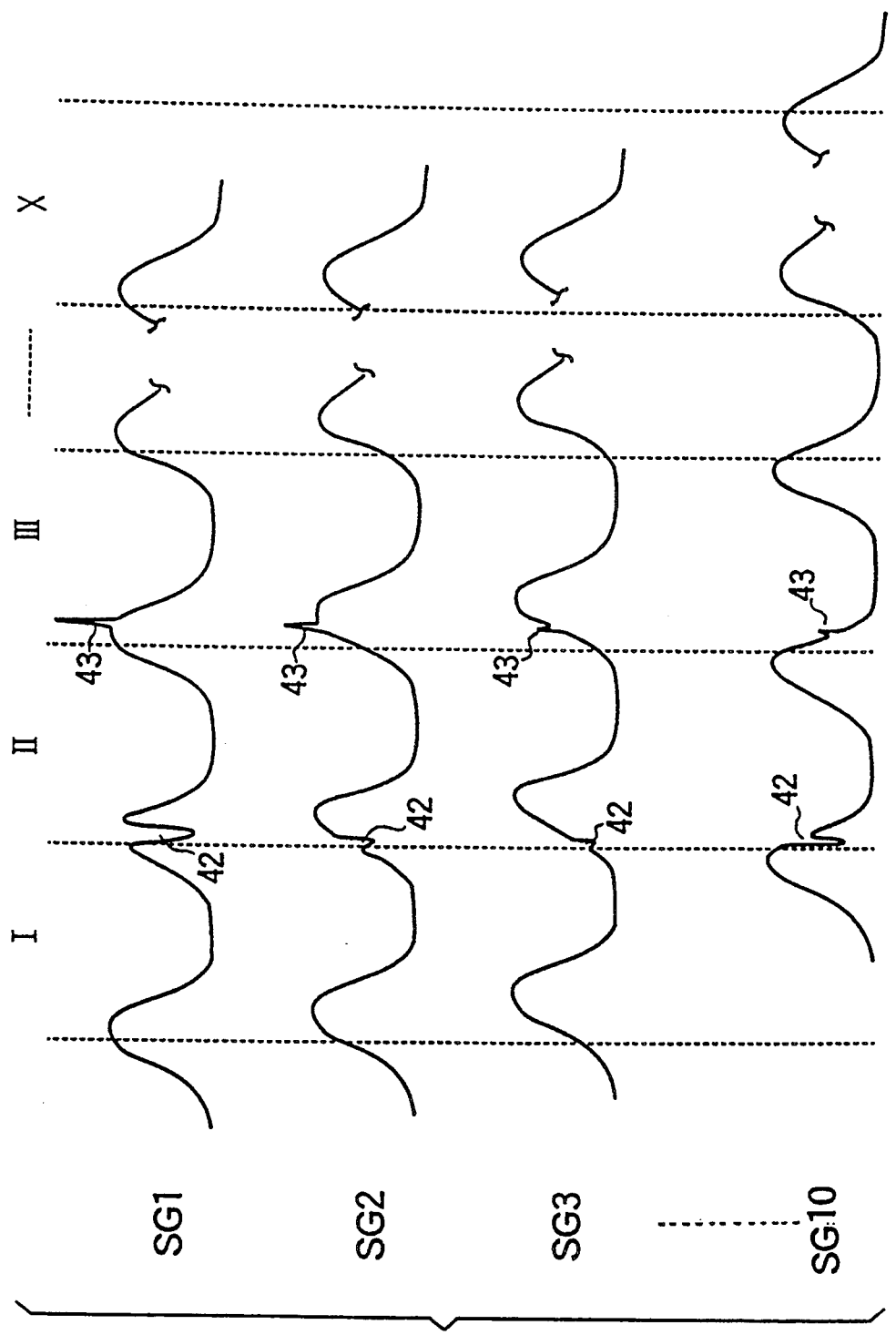
FIG. 5 is a diagram illustrating an example of waveforms of electrical signals SG1–SG10.

Typical waveforms of the output signals SG1–SG10 of the photomultipliers obtained by scanning the glass plate 10 with the laser spot 26 in the X-axis direction and receiving the transmitted light by the light receptor 32 are shown in FIG. 5. The output signals SG1–SG10 have shifted the phases thereof corresponding to the arranged spacings of the optical fibers 34. Where flaws exist in the glass plate 10, spikes in the negative or positive direction are generated at positions corresponding to the positions of the flaws. In the Figure, a negative-direction spike is indicated by reference numeral 42 and a positive-direction spike by reference numeral 43.

Figure 6:
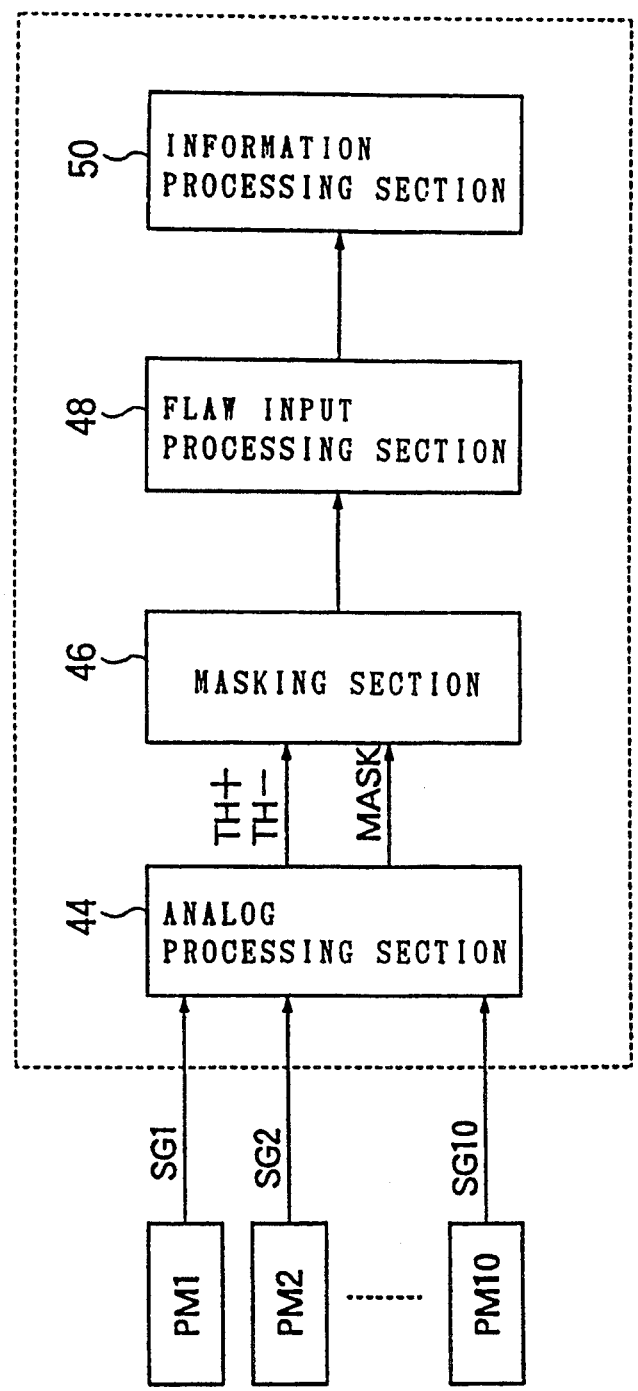
FIG. 6 is a diagram illustrating the basic construction of an electrical system for detecting flaws by fetching electrical signals from photomultipliers.

Next, an electrical system for detecting flaws by fetching the aforementioned electrical signals will be described according to FIG. 6. The electrical system comprises an analog processing section 44 that processes the electrical signals SG1–SG10 output by the photomultipliers PM1–PM10, producing flaw information signals (TH+, TH−, MASK), a masking section 46 that reads mask signals MASK and masks the input signals (TH+, TH−) with a mask pattern corrected by means of software, a flaw input processing section 48 that fetches flaw signals produced by the masking section and signal processing clocks and line synchronization signals, produces from the flaw signals a flaw pattern consisting of bit matrices representing the size of flaws existing in the glass plate 10, and adds positional information to that pattern, and an information processing section 50 that receives flaw patterns and positional information from the flaw input processing section 48, discriminates the size of flaws, and transmits the discrimination results and the positional information to a host information processing system.

Figure 7:
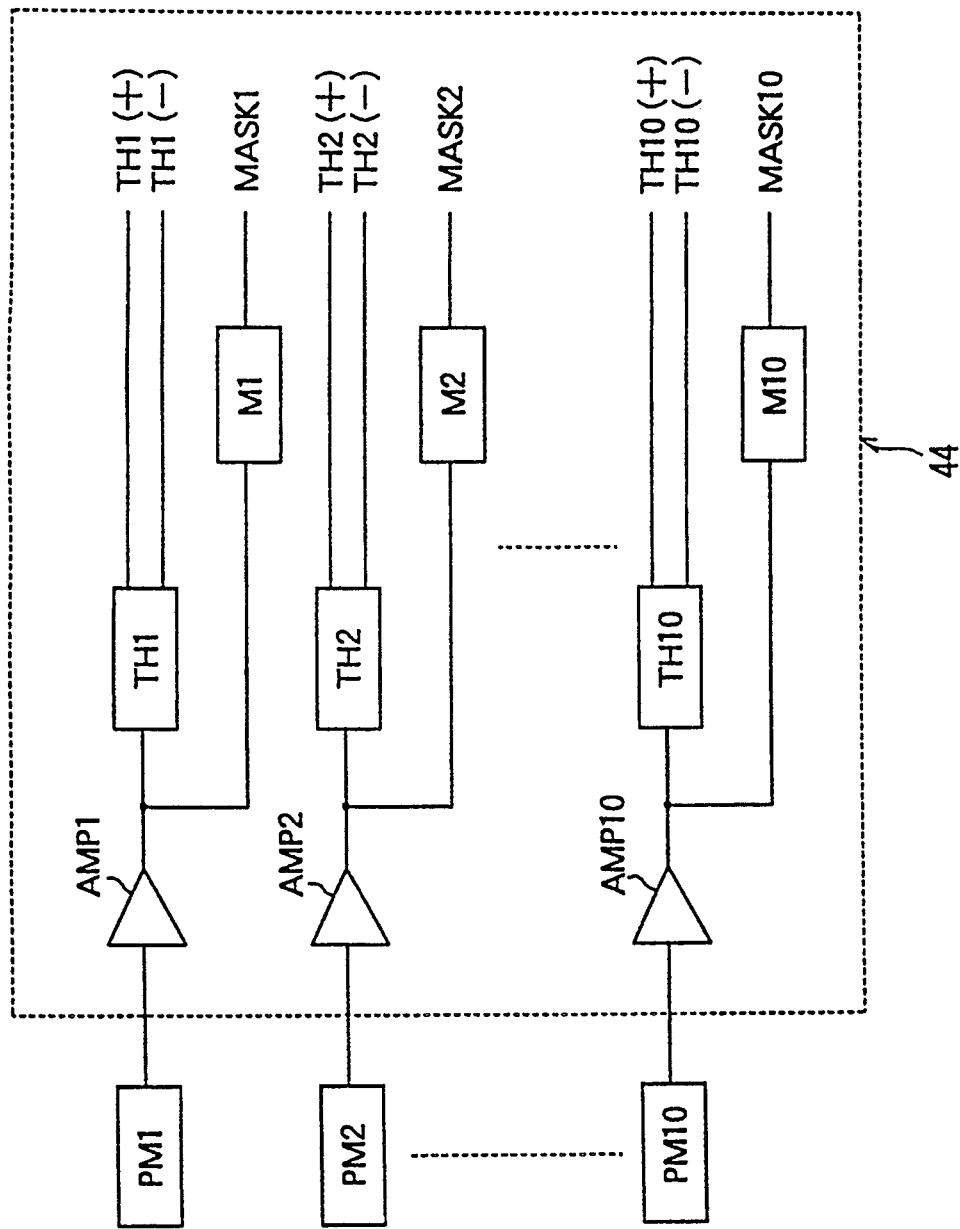
FIG. 7 is a diagram illustrating an example of the construction of an analog processing section.

An example of the construction of the analog processing section 44 is shown in FIG. 7. This section comprises amplifiers AMP1–AMP10 each amplifying the electrical signals SG1–SG10 output by the photomultipliers PM1–PM10, threshold circuits TH1–TH10 slicing the electrical signals by High threshold and Low threshold values, and mask circuits M1–M10 producing mask signals MASK on the pattern level.

Figure 8:
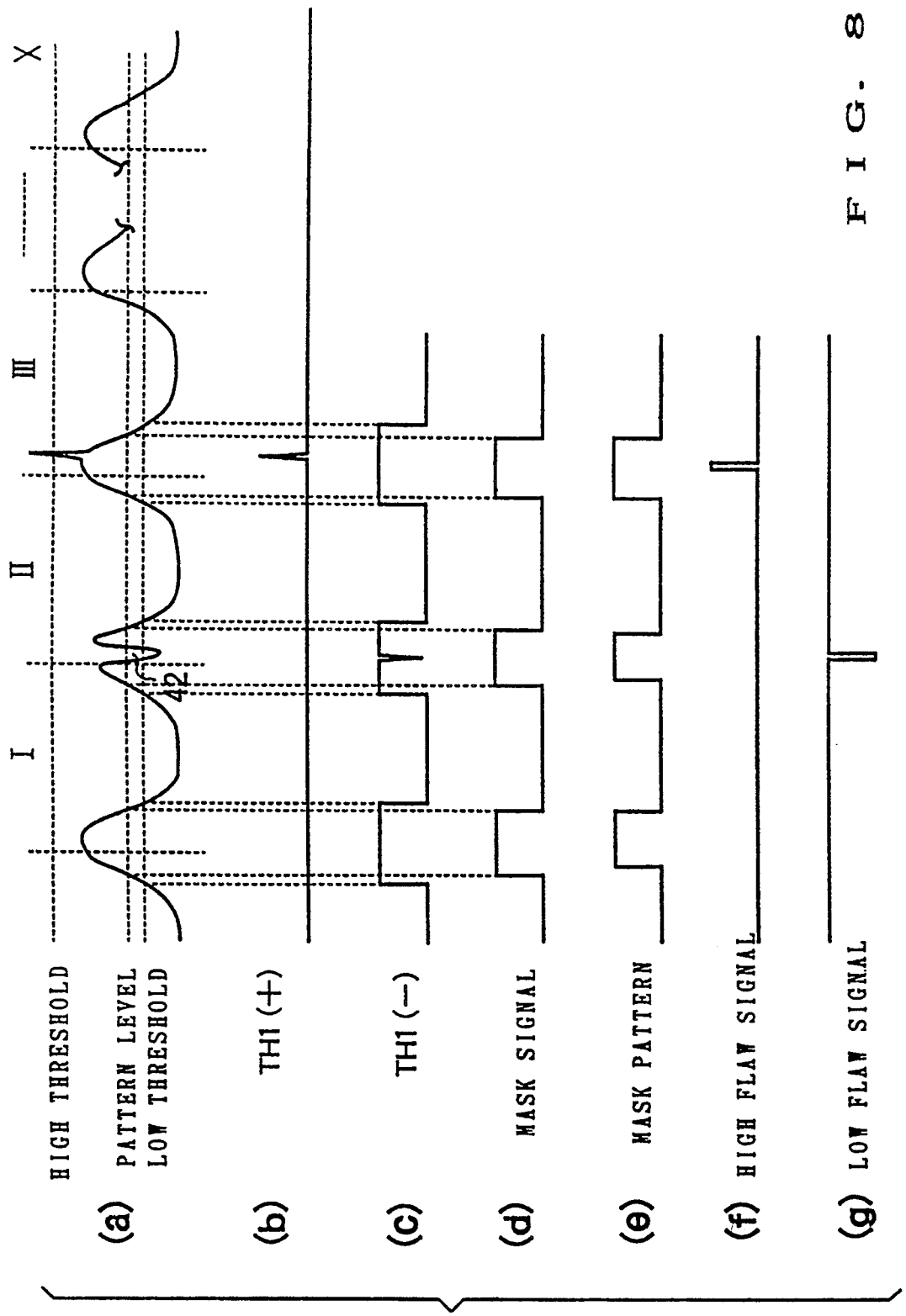
FIG. 8 is a signal waveform diagram of assistance in explaining the operation of the analog processing section and a masking section

Now, the operation of the analog processing section 44 will be described taking the electrical signal SG1 shown in FIG. 5 as an example. FIG. 8 is a signal waveform diagram on which the following description is based.

The electrical signal SG1 having a waveform (a) is amplified by the amplifier AMP1 and input to the threshold circuit TH1 and the mask circuit M1. The threshold circuit TH1 slices the electrical signal SG1 by High and Low threshold values. Waveform (b) represents an output TH1(+) exceeding the High threshold value, and waveform (c) represents an output TH1(−) exceeding the Low threshold value. The mask circuit M1, on the other hand, generates mask signals MASK on the pattern level shown in the waveform (a). Waveform (d) represents a mask signal. These flaw information signals TH(+), TH(−) and MASK are fed to the masking section 46.

Figure 9:
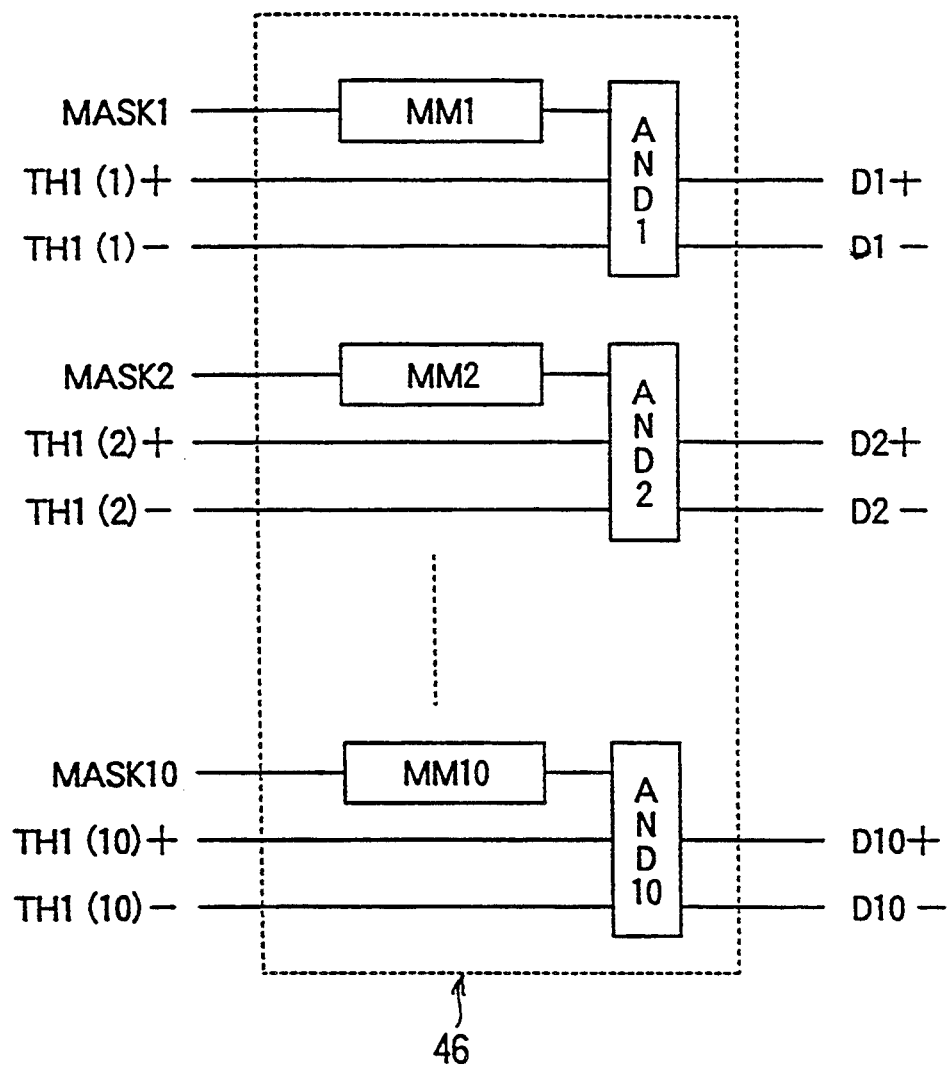
FIG. 9 is a diagram illustrating an example of the construction of the masking section.

FIG. 9 shows the masking section 46. The masking section comprises mask memories MM1-MM10 reading MASK signals and generating MASK patterns corrected by means of software, and AND circuits AND1-AND10 for ANDing MASK patterns and flaw information signals TH+ and TH− for masking. The mask memories MM1-MM10 correct mask signals MASK so as to slightly reduce mask widths and generate MASK patterns. Each AND circuits ANDs a MASK pattern and flaw information signals TH+ and TH− to generate flaw signals D+ and D−. The reason for masking in the aforementioned manner is to produce an input inhibit area by predetermining an inspection range for the flaw detection system so that any particular flaw signal entering from the outside is not identified as a flaw input.

Waveform (e) in FIG. 8 represents a MASK pattern obtained by correcting a MASK1 signal in the mask memory MM1. In the AND circuit 1, the waveforms (b) and (e) are ANDed to output a High flaw signal having a waveform (f). The AND circuit 1 then ANDs the waveforms (c) and (e) to output a Low flaw signal having a waveform (g). These High and Low flaw signals are input to the next-stage flaw input processing section 48. In the following description, flaw signals after masking that were obtained from SG1-SG10 are expressed as $D1\pm-D10\pm$.

Next, the construction of the flaw input processing section 48 will be described.

Figure 10:
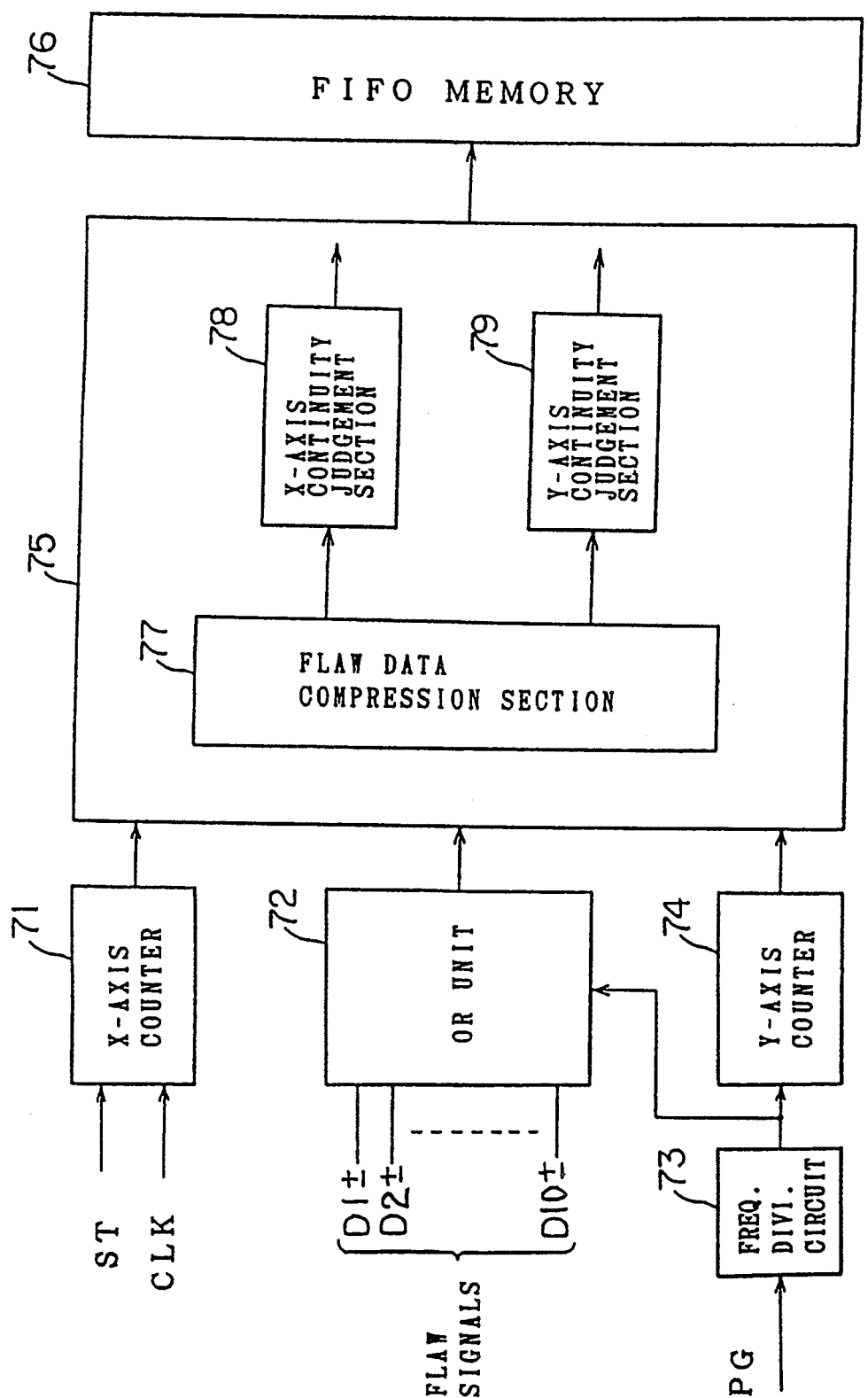
FIG. 10 is a diagram illustrating an example of the construction of a flaw input processing section.

FIG. 10 shows a typical construction of this section. The flaw input processing section 48 comprises an X-axis counter 71, an OR unit 72, a frequency division circuit 73, a Y-axis counter 74, a continuity judgment section 75 and a FIFO memory 76. The continuity judgment section 75 comprises a flaw data compression section 77, an X-axis continuity judgment section 78 and a Y-axis continuity judgment section 79.

The X-axis counter 71 is a counter for counting clocks CLK for X-coordinate division. The X-axis counter 71 is reset by a start pulse ST that is a scanning start signal. The start pulse ST is obtained by receiving the laser beam reflected by the polygonal rotating mirror 22 at a particular position, and subjecting the beam to optical/electrical conversion and waveform shaping. The X-axis counter 71 outputs to the continuity judgment section 75 the counter values at the time when the flaw signals are fetched as the X-coordinate position data.

The OR unit 72 is a unit for accumulating flaw signals $D1\pm-D10\pm$ for a plurality of scans from the masking section 46 to output them at a predetermined timing. Such an OR unit is disclosed in Japanese Patent Publication No. Sho/56(1981)-39419, "Flaw Detector."

The frequency division circuit 73 divides the frequency of a line synchronization signal PG fed from a pulse generator (not shown) that corresponds to the travelling distance of the glass plate in the line direction, and inputs the division results to the OR unit 72, which in turn outputs the accumulated flaw signals to the continuity judgment section 75 at the timing of the frequency-divided line synchronization signal PG.

The Y-axis counter 74 counts the frequency-divided line synchronization signal PG from the frequency division circuit 73, and outputs the count values to the continuity judgment section 75 as the Y-coordinate position data at the time of flaw signal inputting. The Y-axis counter 74 is reset by means of software.

FIG. 11 shows an example of the OR unit 72. The OR unit 72 comprises OR circuits OR1, OR2, - - -, OR10, random access memories RAM1, RAM2, - - -, RAM10, and gate circuits G1, G2, - - -, G10, each corresponding to flaw signals D1, D2, - - -, D10.

Figure 12:
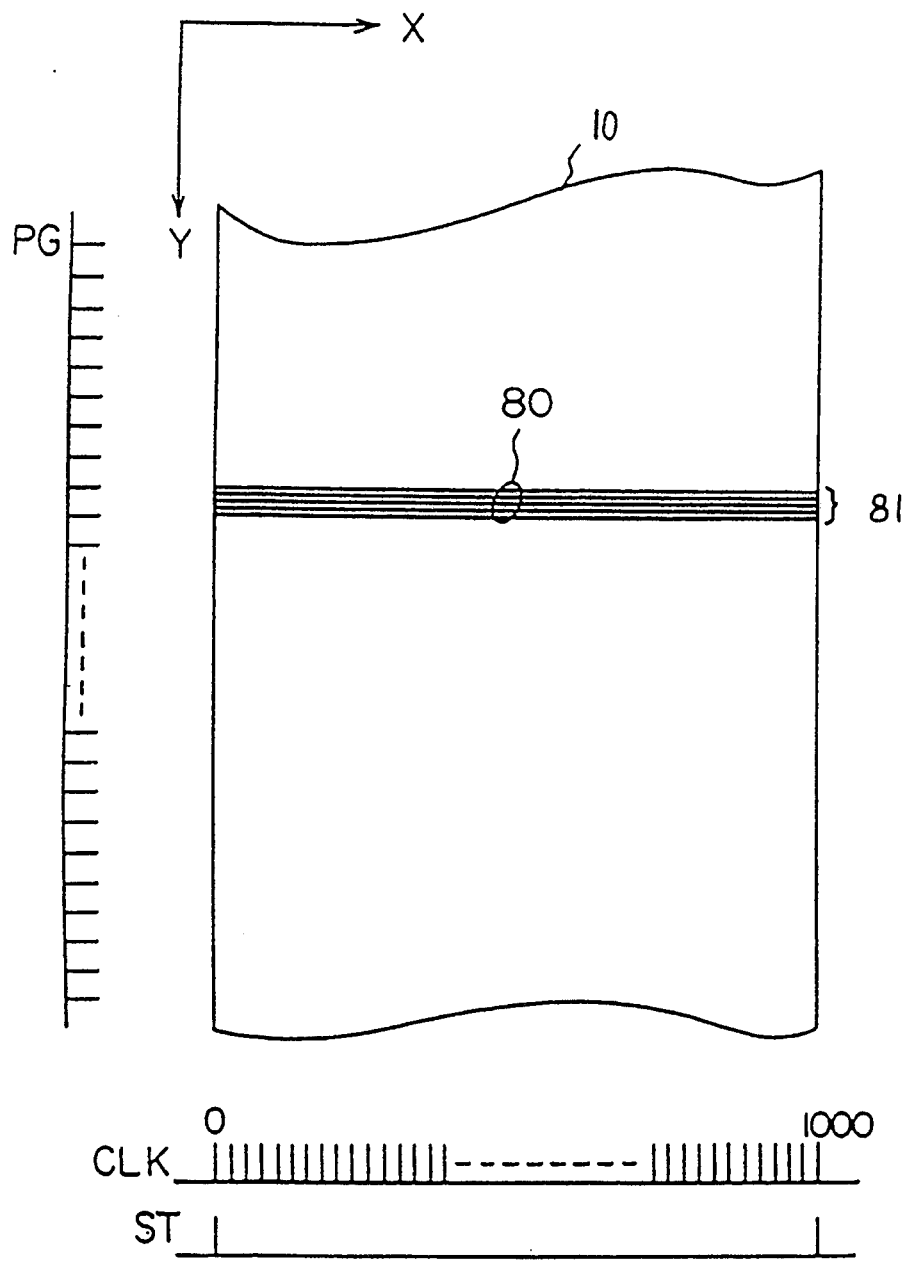
FIG. 12 is a schematic diagram illustrating the relationship between scanning with a laser-beam spot, and clock pulses CLK and line synchronization signals PG after frequency division.
Figure 13:
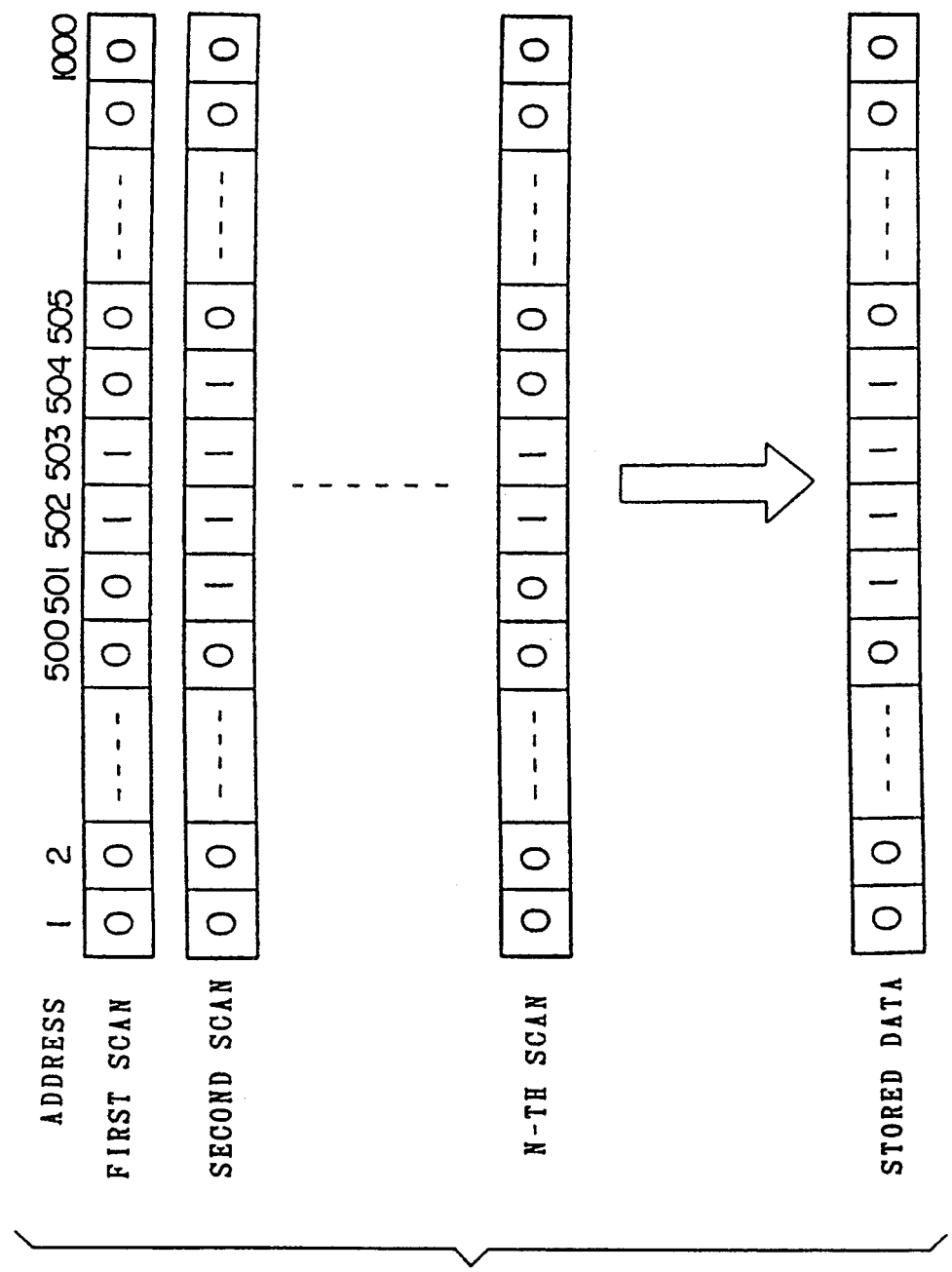
FIG. 13 is a diagram illustrating the state where flaw signals are accumulated in the RAM of an OR unit.

FIGS. 12 and 13 are diagrams of assistance in understanding the operation of the OR unit 72; FIG. 12 being a schematic diagram showing the relationship among scanning with a laser spot, the clocks CLK and the line synchronization signal PG after frequency division, and FIG. 13 being a diagram illustrating the state where flaw signals are accumulated in the RAM1 of the OR unit. In the following, the operation of accumulating a flaw signal D1, for example, in the OR unit 72 will be described, referring to these drawings. It is assumed that the glass plate 10 is scanned n times in the X-axis direction with a laser spot 26 during the duration of a line synchronization signal PG after frequency division. In FIG. 12, numeral 81 refers to n scanning lines. It is also assumed that there are up to 1000 addresses in each RAM of the OR unit 72. The addresses of each RAM correspond to the sequential order of clocks CLK.

As shown in FIG. 12, if there is a "cord" flaw 80 in the glass plate 10, the flaw signal D1 input from the masking section 46 during the first scanning is written in RAM1, and bits "1" are stored in addresses 502 and 503. The flaw signal D1 input from the masking section 46 during the second scanning is ORed with the flaw signal read from the RAM1 in the OR circuit OR1, and then written again in the RAM1, - - -, the flaw signal D1 input during the n-th scanning is ORed with the flaw signal read from the RAM1, and then rewritten in the RAM1. Thus, bits "1" are eventually stored in addresses 501 through 504. In this way, the flaw signals D1 accumulated in the RAM1 are output as flaw data in the continuity judgment section 75 via the gate circuit G1 at the timing of the line synchronization signal PG frequency-divided by the frequency division circuit 73.

The continuity judgment section 75 comprises a flaw data compression section 77 for compressing flaw data from the OR unit 72, an X-axis continuity judgment section 78 for outputting start and end addresses in the X-axis direction by judging the X-axis continuity of the compressed flaw data, and a Y-axis continuity judgment section 79 for outputting start and end addresses in the Y-axis direction by judging the Y-axis continuity of the compressed flaw data.

Now, the operation of the continuity judgment section 75 having the aforementioned construction will be described, referring to FIGS. 14 and 15. FIG. 14 is a diagram of assistance in explaining the concept of the operation of the flaw data compression section 77 compressing flaw data, and FIG. 15 is a diagram illustrating typical bit matrices of the compressed flaw data to explain the operation of the X-axis continuity judgment section 78 and the Y-axis continuity judgment section 79.

As flaw data D1, D2, - - -, D10 are output from the OR unit, the flaw data have two-dimensional bit matrices in the X-axis address and Y-axis address directions, as shown in FIG. 14. Now, assuming a three-dimensional space, in which these flaw data D1, D2, - - -, D10 having two-dimensional bit matrices are arranged in the Z-axis direction, it can be considered that three-dimensional flaw data groups D1, D2, - - -, D10 are output from the OR unit 72. The flaw data compression section 77 ORs in the z-axis direction all the three-dimensional flaw data groups D1, D2, - - -, D10 having data matrices arranged in the X-axis and Y-axis addresses to obtain compressed two-dimensional flaw data DB. In FIG. 14, bits "1" are present only in the flaw data D1 and D10.

FIG. 15 shows typical bit matrices of the flaw data compressed on the basis of the aforementioned concept.

The X-axis continuity judgment section 78 and the Y-axis continuity judgment section 79 check bits "1" for continuity in the X-axis and Y-axis directions to detect the discontinuity of the bits "1," and determine whether the detected discontinuity is to be connected in the X-axis and Y-axis directions, depending on the parameters involved.

Figure 15A:
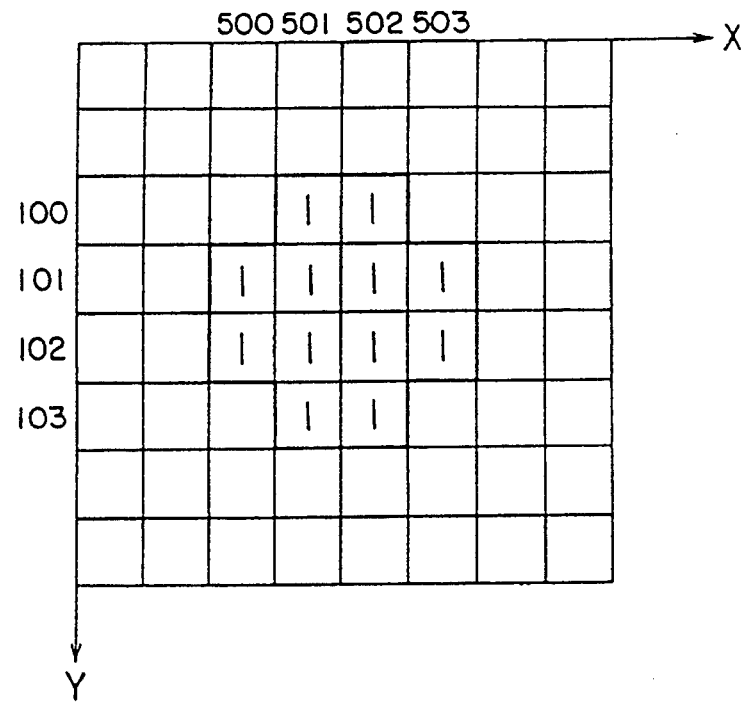
FIGS. 15A and 15B are diagrams illustrating examples of bit matrices of flaw data after compression.

FIG. 15A shows a flaw data block synthesized through continuity judgment when parameters for both the X-axis continuity judgment section 78 and the Y-axis continuity judgment section 79 are 0. Address 500 is output as the X-axis start address of this flaw data block, and address 503 is output as the X-axis end address thereof from the X-axis continuity judgment section 78. From the Y-axis continuity judgment section 79, on the other hand, address 100 is output as the Y-axis start address of this flaw data block, and address 103 is output as the Y-axis end address thereof.

Figure 15B:
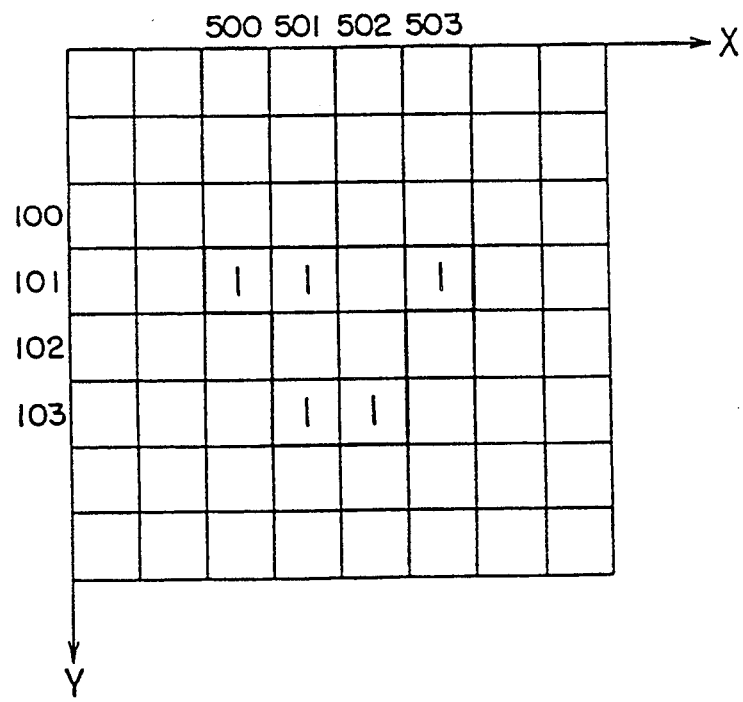

FIG. 15B shows a flaw data block synthesized through continuity judgment when parameters for both the X-axis continuity judgment section 78 and the Y-axis continuity judgment section 79 are 1. When the parameters are 1, a flaw data block as shown in the figure is synthesized, even if bits "1" are discontinued, by connecting the discontinuity. In this case, address 500 is output as the X-axis start address of this flaw data block, and address 503 is output as the X-axis end address thereof from the X-axis continuity judgment section 78. From the Y-axis continuity judgment section 79, on the other hand, address 101 is output as the Y-axis start address of the flaw data block, and address 103 is output as the Y-axis end address thereof. In this way, when a shift occurs in the timing at which flaw signals are generated by a plurality of photomultipliers during the scanning of one flaw with a laser spot, these shifted flaw signals can be identified as flaw data from that flaw by performing continuity judgment that Connects discontinuities in bits "1" through interpolation.

When the continuity of bits "1" is found discontinued during judgment by the Y-axis continuity judgment section 79, the X-axis start and end addresses and the Y-axis start and end addresses of the flaw data block are output to the FIFO memory 76 as the information on flaw position from the X-axis continuity judgment section 78 and the Y-axis continuity judgment section 79. In the meantime, the Y-axis continuity judgment section 79 has a function of outputting the information on flaw pattern and position to the FIFO memory 76 by forcibly cutting the Y-axis continuity of bits "1" which has lasted longer than a predetermined length.

The FIFO memory 76 stores the transmitted information on flaw position to transfer to the memory of the information processing section through direct memory access.

The information processing section 50 discriminates the size and position of a flaw on the basis of the information on flaw pattern and position transmitted by the flaw input processing section 48, and transmits these discrimination results to a host information processing system, which in turn controls the manufacturing line process and the plate cutting process on the basis of the transmitted information.

Although description has been made in the foregoing on a discriminating type flaw detection system for glass plate, this invention is not limited to this embodiment, various modifications and alterations are of course possible without departing from the spirit and the scope of this invention.

The invention claimed is:

1. A flaw detection system for detecting flaws in a light-transmitting plate material which has first and second planar faces and which is moving through the system in a travelling direction, the system comprising:
    a scanner for scanning the first planar face of the light-transmitting plate material with a beam spot in a direction orthogonal to the travelling direction of said light-transmitting plate material,
    a light receptor for receiving light of the beam spot transmitted through said light-transmitting plate material from the first planar face to the second planar face, the light receptor comprising an optical-fiber array in which multiple optical fibers are arranged linearly in the direction orthogonal to said travelling direction, and
    n photoelectric converters, ordinally numbered first through nth, n being an integer greater than two,
    wherein the optical-fiber array includes a plurality of contiguous divisions each of said divisions having n successive ones of the multiple optical fibers which n successive fibers are ordinally numbered first through nth, the n optical fibers in each of said divisions being coupled to respective ones of said n photoelectric converters.

2. A flaw detection system for light-transmitting plate materials as set forth in claim 1 wherein:
    the first and second faces of the light transmitting plate material divide the system into respective first and second sides, such that the scanner is in the first side of the system and the light receptor is in the second side, and
    the beam spot is formed by a beam of light having a beam waist which is located in the first side of the system.

3. A flaw detection system for light-transmitting plate materials as set forth in claim 1 wherein:
    the first and second faces of the light transmitting plate material divide the system into respective first and second sides, such that the scanner is in the first side of the system and the light receptor is in the second side, and
    the beam spot is formed by a beam of light having a beam waist which is located in the second side of the system.

4. A flaw detection system for light-transmitting plate materials as set forth in claim 2 or 3 wherein said flaw detection system comprises:
    an analog processing section which generates n flaw information signals, indicating a flaw present in said light-transmitting plate material, and n respective mask signals by processing n electrical signals provided by the n photoelectric converters respectively,
    a masking section which generates n flaw signals by
    a) modifying the n mask signals to form n mask patterns and b) masking said n flaw information signals on the basis of said n mask patterns respectively to generate said n flaw signals, and a flaw input processing section which fetches said flaw signals for compression and continuity judgment.

5. A flaw detection system for light-transmitting plate materials as set forth in claim 4 wherein said analog processing section comprises:

n amplifiers each amplifying electrical signals from a respectively different one of said n photoelectric converters to produce n amplified electrical signals, respectively, n threshold circuits which process the n amplified electrical signals by slicing respectively different ones of said n amplified electrical signals on the basis of respective predetermined High threshold and Low threshold values to generate the n flaw information signals, and n mask circuits for generating said mask signals from said n amplified electrical signals respectively.

6. A flaw detection system for light-transmitting plate materials as set forth in claim 5 wherein said masking section comprises:

n mask memories which modify respective ones of said n mask signals by slightly reducing, in pulse width, pulse signals which form the mask signals to generate the n mask patterns, and n AND circuits which generate said flaw signals by ANDing respective ones of the flaw information signals provided by said n threshold circuits with respective ones of said n mask patterns provided by said n mask memories.

7. A flaw detection system for light-transmitting plate materials as set forth in claim 6 wherein said flaw input processing section comprises:

a first counter which counts a first pulse train relating to a position in the direction orthogonal to the travelling direction of said light-transmitting plate material to output a first count value obtained when said flaw signals are fetched, a second counter which counts a second pulse train relating to a position in the travelling direction of said light-transmitting plate material to output a second count value obtained when said flaw signals are fetched, an OR unit which accumulates and ORs flaw signals for a plurality of scanning operations to output flaw data at instants in time determined by said second pulse train, a continuity judgment circuit which compresses flaw data from said OR unit and which judges said compressed flaw data for continuity in said travelling direction and in said direction orthogonal to said travelling direction to produce continuity output signals, and a buffer memory which temporarily stores said continuity output signals.

* * * * *